(12) United States Patent
Wang et al.

(10) Patent No.: US 9,551,850 B2
(45) Date of Patent: Jan. 24, 2017

(54) LIGHT SOURCE MODULE OF OPTICAL APPARATUS AND OPERATING METHOD THEREOF

(71) Applicants: Crystalvue Medical Corporation, Taoyuan (TW); Sheng-Lung Huang, Taipei (TW)

(72) Inventors: William Wang, Taoyuan (TW); Chung-Ping Chuang, Taoyuan (TW); Meng-Shin Yen, Taipei (TW); Chung-Cheng Chou, Luzhu Township, Taoyuan County (TW); Sheng-Lung Huang, Taipei (TW); Kuang-Yu Hsu, Taipei (TW); Chien-Chung Tsai, Taipei (TW); Tuan-Shu Ho, Taipei (TW)

(73) Assignees: CRYSTALVUE MEDICAL CORPORATION, Taoyuan (TW); Sheng-Lung Huang, Taipei (TW)

( * ) Notice: Subject to any disclaimer, the term of this patent is extended or adjusted under 35 U.S.C. 154(b) by 195 days.

(21) Appl. No.: 14/485,432

(22) Filed: Sep. 12, 2014

(65) Prior Publication Data

US 2015/0078705 A1    Mar. 19, 2015

(30) Foreign Application Priority Data

Sep. 14, 2013  (TW) .............................. 102133383 A

(51) Int. Cl.
| | | |
|---|---|---|
| *G02B 6/42* | (2006.01) | |
| *A61B 3/00* | (2006.01) | |
| *H01S 3/067* | (2006.01) | |
| *H01S 3/094* | (2006.01) | |
| *H01S 3/0941* | (2006.01) | |
| *H01S 3/16* | (2006.01) | |

(52) U.S. Cl.
CPC .......... *G02B 6/4296* (2013.01); *A61B 3/0008* (2013.01); *G02B 6/4204* (2013.01); *H01S 3/06795* (2013.01); *G02B 6/4212* (2013.01); *H01S 3/09415* (2013.01); *H01S 3/094007* (2013.01); *H01S 3/1618* (2013.01)

(58) Field of Classification Search
CPC ... G02B 6/4204; G02B 6/4212; G02B 6/4296; A61B 3/008; H01S 3/06795; H01S 3/09415

See application file for complete search history.

(56) References Cited

U.S. PATENT DOCUMENTS

| | | | | |
|---|---|---|---|---|
| 4,835,778 A | * | 5/1989 | Kafka | ...................... H01S 3/067 372/6 |
| 5,166,940 A | * | 11/1992 | Tumminelli | .......... H01S 3/0675 372/6 |

(Continued)

*Primary Examiner* — Daniel Petkovsek

(74) *Attorney, Agent, or Firm* — Muncy, Geissler, Olds & Lowe, P.C.

(57) ABSTRACT

A light source module of an optical apparatus is disclosed. The light source module includes a laser pump unit, a lens unit, and a fiber unit. The laser pump unit generates a laser source. The lens unit converts the laser source into a condensed beam. The fiber unit receives the condensed beam and emits an optical signal. The light source module can achieve effects of low cost, large bandwidth, high resolution, and high stability with well-designed pump power of the laser pump unit, and length, doping material, and core size of the fiber unit.

18 Claims, 1 Drawing Sheet

(56) References Cited

U.S. PATENT DOCUMENTS

| | | | | |
|---|---|---|---|---|
| 5,652,756 | A * | 7/1997 | Stultz | H01S 3/067 372/10 |
| 6,233,259 | B1 * | 5/2001 | Ventrudo | G02B 6/02076 372/108 |
| 7,120,340 | B2 * | 10/2006 | Berkey | C03B 37/01217 359/333 |
| 8,824,519 | B1 * | 9/2014 | Seurin | H01S 5/4012 372/101 |
| 2003/0165008 | A1 * | 9/2003 | Rice | H01S 3/06754 359/341.1 |
| 2010/0260210 | A1 * | 10/2010 | Spinelli | H01S 3/067 372/6 |
| 2011/0128611 | A1 * | 6/2011 | Lin | G02B 6/0003 359/326 |
| 2015/0029819 | A1 * | 1/2015 | Yacoubian | G01N 21/171 367/7 |
| 2015/0077709 | A1 * | 3/2015 | Wang | A61B 3/0008 351/221 |

* cited by examiner

LIGHT SOURCE MODULE OF OPTICAL APPARATUS AND OPERATING METHOD THEREOF

BACKGROUND OF THE INVENTION

1. Field of the Invention

This invention relates to optical detection, especially to a light source module of an optical apparatus and an operating method thereof applied to ophthalmology detection to achieve effects of low cost, large bandwidth, high resolution, and high stability.

2. Description of the Prior Art

In recent years, with the progress of optical detection technology, non-invasive optical detection apparatuses and methods are provided to detect the structure and composition of the tissue of the object to be detected; for example, it can be widely used in functional detection and medical diagnosis of human body. Especially, compared to other organs of human body, the eyes and their surrounding tissues have characteristics of high transparency and vulnerability to injury; therefore, the optical detection technology is suitable to be widely applied in ophthalmology detection apparatuses, such as an optometry machine, a tonometer, a fundus Camera, a corneal thickness meter, and an optical tomography scanner.

However, in practical applications, when the conventional optical ophthalmology detection apparatus is used to emit incident light is emitted to the tissues in the eyes, the different tissues may have different optical characteristics (e.g., reflection, scattering, refraction, or absorption), and the conventional optical ophthalmology detection apparatus may obtain detection results having poor resolution or even misjudgments.

In addition, since the laser has many advantages of beam straightness, single wavelength, and high coherence, it is usually used in the conventional optical ophthalmology detection apparatus. For example, a super luminescent diode (SLD) is usually used as the light source of the conventional optical ophthalmology detection apparatus. Although the SLD light source of the conventional optical ophthalmology detection apparatus can provide good bandwidth and resolution, it still has many disadvantages of high cost, high degree of decay with time, and system instability needed to be overcome.

Therefore, the invention provides a light source module of an optical apparatus and an operating method thereof to solve the above-mentioned problems.

SUMMARY OF THE INVENTION

An embodiment of the invention is a light source module of an optical apparatus. In this embodiment, the optical apparatus is applied to ophthalmology detection. The light source module includes a laser pump unit, a lens unit, and a fiber unit. The laser pump unit generates a laser source. The lens unit converts the laser source into a condensed beam. The fiber unit receives the condensed beam and emits an optical signal. The light source module can achieve effects of low cost, large bandwidth, high resolution, and high stability with well-designed pump power of the laser pump unit, and length, doping material, and core size of the fiber unit.

In an embodiment, the laser pump unit having a core pump structure needs a pump power ranging from 30 mW to 300 mW; the laser pump unit having a cladding pump structure needs the pump power ranging from 100 mW to 10 W.

In an embodiment, the lens unit includes gradient-index (GRIN) lens.

In an embodiment, the fiber unit includes an Yb-doped double-clad fiber, an Er-doped double-clad fiber, or a Tm-doped double-clad fiber.

In an embodiment, a length of the fiber unit is related to a pump structure, a concentration of Yb ion in an Yb-doped fiber, and a core diameter.

In an embodiment, a core diameter of the laser pump unit having a core pump structure ranges from 3 um to 20 um; the core diameter of the laser pump unit having a cladding pump structure ranges from 10 um to 40 um.

In an embodiment, the light source module further includes a filter unit. The filter unit is disposed between the lens unit and the fiber unit and used for filtering the condensed beam before the condensed beam enters into the fiber unit.

In an embodiment, the light source module further includes an output end and a filter unit. The output end is used for outputting the optical signal. The filter unit is disposed between the fiber unit and the output end and used for enhancing an amplified spontaneous emission (ASE) of a forward direction from the lens unit toward the fiber unit by reflecting the amplified spontaneous emission of a reverse direction from the fiber unit toward the lens unit back to the fiber unit when the fiber unit receives the condensed beam.

In an embodiment, when the laser pump unit has a core pump structure, the optical signal is an amplified spontaneous emission (ASE) outputted by a core of the fiber unit; when the laser pump unit has a cladding pump structure, the optical signal is a spontaneous emission collected and outputted by a cladding layer having larger numerical aperture of the fiber unit and the optical signal is not amplified by stimulated emission to maintain a large bandwidth the same with fluorescence.

Another embodiment of the invention is a light source module operating method. In this embodiment, the light source module operating method is used for operating a light source module. The light source module includes a laser pump unit, a lens unit, and a fiber unit. The method includes steps of: (a) the laser pump unit generating a laser source; (b) the lens unit converting the laser source into a condensed beam; and (c) the fiber unit receiving the condensed beam and emitting an optical signal.

Compared to the prior art, the light source module of the optical apparatus and the operating method thereof in the invention have many advantages of:

(1) providing bandwidth and resolution similar to those of the SLD light source;

(2) low cost;

(3) low degree of decay with time and good system stability.

The advantage and spirit of the invention may be understood by the following detailed descriptions together with the appended drawings.

BRIEF DESCRIPTION OF THE APPENDED DRAWINGS

DETAILED DESCRIPTION OF THE INVENTION

A preferred embodiment of the invention is a light source module of an optical apparatus. In this embodiment, the optical apparatus can be an optical ophthalmology detection apparatus, but not limited to this.

Figure 1:
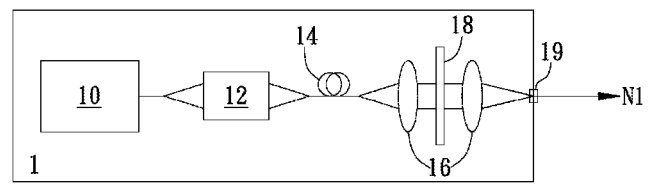
FIG. 1 illustrates a functional block diagram of the light source module of the optical apparatus in an embodiment of the invention.

Please refer to FIG. 1. FIG. 1 illustrates a functional block diagram of the light source module of the optical apparatus in this embodiment. As shown in FIG. 1, the light source module 1 includes a laser pump unit 10, a GRIN lens 12, a fiber unit 14, a lens set 16, a filter unit 18, and an output end 19. Wherein, the GRIN lens 12 is disposed between the laser pump unit 10 and the fiber unit 14; the fiber unit 14 is disposed between the GRIN lens 12 and the lens set 16; the filter unit 18 is disposed between two lenses of the lens set 16.

In this embodiment, the laser pump unit 10 is used to generate a laser light source. The GRIN lens 12 is used to convert the laser light source into a condensed beam. The fiber unit 14 is used to receive the condensed beam and emit an optical signal. It should be noticed that the light source module 1 of the optical apparatus in the invention has appropriate designs of the pump power of the laser pump unit 10 and the length, dopant, and core size of the fiber unit 14, so that the effects of low cost, large bandwidth, high resolution, and high stability can be achieved when the optical apparatus is operated.

The laser pump unit 10 includes laser diodes (LDs). In the laser material, electrons at low energy levels are elevated to high energy levels, so that the number of the electrons at high energy levels is larger than that at low energy levels to form a condition of particle number inversion. When external photons is emitted to the laser material, the electrons at high energy levels will be affected by the external photons and down to low energy levels, and photons having the same phase and wavelength with the external photons will be generated when the electrons move from the high energy levels to the low energy levels; therefore, the laser pump unit 10 can emit the laser light source.

In practical applications, the laser pump unit 10 can be driven by current, heat, or laser having other wavelength, but not limited to this. If the laser pump unit 10 has a core pump structure, the pump power of the laser pump unit 10 ranges from 30 mW to 300 mW; if the laser pump unit 10 has a cladding pump structure, the pump power of the laser pump unit 10 ranges from 100 mW to 10 W, but not limited to this.

The laser diodes used in the laser pump unit 10 can be TO-CAN package type laser diodes, such as transistor-outline package type, dual-in-line package type, or butterfly package type, but not limited to this. Wherein, the butterfly package type laser diodes have advantages of large housing area, good cooling effect, transmission in different rate, and long-distance transmission.

In this embodiment, the GRIN lens 12 disposed between the laser pump unit 10 and the fiber unit 14 is used to couple the laser light source and the fiber unit 14 and increase their coupling efficiency. The GRIN lens 12 has many advantages of: (1) having different focal lengths to be chosen; (2) easy use and coupling calibration; (3) small volume and light weight; (4) low cost; (5) small image distortion.

In fact, the GRIN lens 12 can be a rod-shaped GRIN lens having 0.29 spacing, and GRIN lens 12 converts the laser light source emitted from the laser pump unit 10 into the condensed beam and then the condensed beam is emitted to the fiber unit 14, so that the coupling efficiency between the laser light source of the laser pump unit 10 and the fiber unit 14 can be enhanced.

In general, the material of the fiber unit 14 is glass fiber including the core in the interior of the fiber unit 14 and the cladding layer in the external part of the fiber unit 14. The core has larger index of refraction than the cladding layer does; therefore, when a light is emitted into the fiber unit 14, a total reflection of the light will be occurred between the core and the cladding layer to guide the light.

In this embodiment, the fiber unit 14 can include fibers doped by other materials, such as an Yb-doped double-clad fiber, an Er-doped double-clad fiber, or a Tm-doped double-clad fiber. If the core pump structure and Yb1200-6/125 DC fiber are used, the fiber length of the fiber unit 14 ranges from 3 cm to 30 cm; if the cladding pump structure and Yb1200-20/125 DC fiber are used, the fiber length of the fiber unit 14 ranges from 15 cm to 1 m. If the core pump structure is used, the core diameter of the fiber unit 14 ranges from 3 um to 20 um; if the cladding pump structure is used, the core diameter of the fiber unit 14 ranges from 10 um to 40 um.

After the fiber unit 14 receives the condensed beam from the GRIN lens 12 and emits the optical signal, the optical signal will be filtered by the filter unit 18 and the output end 19 will output the filtered first optical signal N1. In fact, the filter unit 18 can be a high-pass filter, low-pass filter, band-pass filter, or any other types of filter without any specific limitations.

It should be noticed that the filter unit 18 can be not only disposed between the fiber unit 14 and the output end 19, but also disposed between the fiber unit 14 and the GRIN lens 12 to enhance an amplified spontaneous emission (ASE) of a forward direction from the GRIN lens 12 toward the fiber unit 14 by reflecting the amplified spontaneous emission of a reverse direction from the fiber unit 14 toward the GRIN lens 12 back to the fiber unit 14 when the fiber unit 14 receives the condensed beam, but not limited to this.

Figure 2:
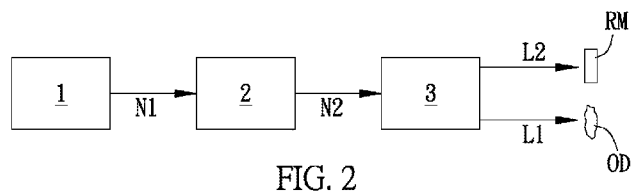
FIG. 2 illustrates a functional block diagram of the optical apparatus OA including the light source module 1.

In an embodiment, as shown in FIG. 2, the optical apparatus OA includes the light source module 1, an optical module 2, and an interference module 3. The optical module 2 is disposed between the light source module 1 and the interference module 3. The light source module 1 is used to emit the first optical signal N1 as mention above. The optical module 2 includes fibers and lens. The optical module 2 is used to receive the first light signal N1 from the light source module 1 and emit a second light signal N2. The interference module 3 is used to receive the second light signal N2 from the optical module 2 and provide a first incident light L1 and a second incident light L2 to an object OD to be detected and a reference mirror RM respectively.

In practical applications, the optical module 2 can include a collimating lens and a multi-mode fiber used to generate the second light signal N2 according to the first light signal N1. In this embodiment, a core of the multi-mode fiber used in the optical module 2 can have a diameter of 200 um, but not limited to this.

In this embodiment, the interference module 3 can have an interference optical path used to receive the second light signal N2 from the optical module 2 and generate the first incident light L1 and the second incident light L2 according to the second light signal N2. In fact, the first incident light L1 that the interference module 3 provides to the object OD to be detected can have a central frequency of 1030 nm, a bandwidth wider than 45 nm, and an axial resolution smaller than 10 um, but not limited to this.

The multi-mode fiber of the optical module 2 can transmit the optical signal through the core or the cladding layer. If the multi-mode fiber transmits the optical signal through the core, the first incident light L1 that the interference module 3 provides to the object OD to be detected can have the central frequency of 1030 nm, the bandwidth of 19 nm, and the axial resolution of 22 um. If the multi-mode fiber transmits the optical signal through the cladding layer, the first incident light L1 that the interference module 3 provides to the object OD to be detected can have the central frequency of 1030 nm, the bandwidth of 47 nm, and the axial resolution of 9.1 um.

According to the above-mentioned measurement results, it can be found that the central frequency of the first incident light L1 when the multi-mode fiber transmits the optical signal through the cladding layer is equal to the central frequency of the first incident light L1 when the multi-mode fiber transmits the optical signal through the core, but the bandwidth of the first incident light L1 when the multi-mode fiber transmits the optical signal through the cladding layer is obviously larger than the bandwidth of the first incident light L1 when the multi-mode fiber transmits the optical signal through the core, and the axial resolution of the first incident light L1 when the multi-mode fiber transmits the optical signal through the cladding layer is obviously better (smaller value) than the axial resolution of the first incident light L1 when the multi-mode fiber transmits the optical signal through the core. Therefore, the user can control the multi-mode fiber to transmit the optical signal through the cladding layer or the core based on practical needs.

In practical applications, the optical apparatus of the invention can achieve high output power (1.2 MW) and large bandwidth (47 nm). In addition, the reference mirror RM can be a conventional flat surface reference mirror or a curved surface reference mirror. When the curved surface reference mirror is used as the reference mirror RM, the iris size and the signal-noise ratio (SNR) will be increased.

Another embodiment of the invention is a light source module operating method. In this embodiment, the light source module operating method is used for operating a light source module. The light source module includes a laser pump unit, a lens unit, and a fiber unit.

Figure 3:
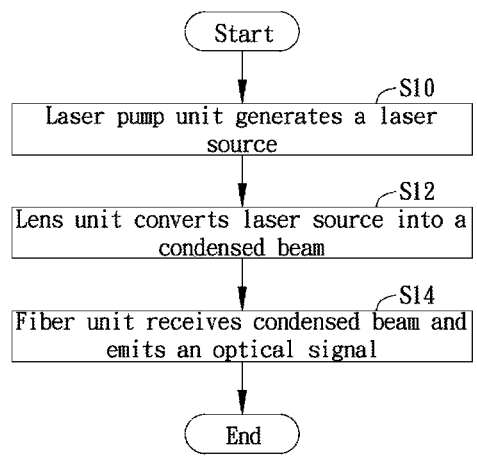
FIG. 3 illustrates a flowchart of the method of operating the light source module of the optical apparatus in another embodiment of the invention.

Please refer to FIG. 3. FIG. 3 illustrates a flowchart of the light source module operating method in this embodiment. As shown in FIG. 3, in the step S10, the laser pump unit generates a laser source; in the step S12, the lens unit converts the laser source into a condensed beam; in the step S14, the fiber unit receives the condensed beam and emits an optical signal.

In practical applications, the method can enhance an amplified spontaneous emission (ASE) of a forward direction from the lens unit toward the fiber unit by reflecting the amplified spontaneous emission of a reverse direction from the fiber unit toward the lens unit back to the fiber unit when the fiber unit receives the condensed beam, or filter the optical signal after the fiber unit emits the optical signal.

In this embodiment, if the laser pump unit has a core pump structure, the pump power of the laser pump unit ranges from 30 mW to 300 mW; if the laser pump unit has a cladding pump structure, the pump power of the laser pump unit ranges from 100 mW to 10 W. The lens unit includes gradient-index (GRIN) lens. The fiber unit includes an Yb-doped double-clad fiber, an Er-doped double-clad fiber, or a Tm-doped double-clad fiber. If the core pump structure and Yb1200-6/125 DC fiber are used, the fiber length of the fiber unit ranges from 3 cm to 30 cm; if the cladding pump structure and Yb1200-20/125 DC fiber are used, the fiber length of the fiber unit ranges from 15 cm to 1 m. If the core pump structure is used, the core diameter of the fiber unit ranges from 3 um to 20 um; if the cladding pump structure is used, the core diameter of the fiber unit ranges from 10 um to 40 um.

Compared to the prior art, the light source module of the optical apparatus and the operating method thereof in the invention have many advantages of:

(1) providing bandwidth and resolution similar to those of the SLD light source;

(2) low cost;

(3) low degree of decay with time and good system stability.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. A light source module, applied in an optical apparatus, the optical apparatus comprising an optical module and an interference module, and the optical module being disposed between the light source module and the interference module, the optical module comprising a collimating lens and a multi-mode fiber, the light source module comprising:

a laser pump unit comprising a butterfly package type laser diode, for generating a laser source;

a lens unit, for converting the laser source into a condensed beam; and a fiber unit, for receiving the condensed beam and emitting a first optical signal to the optical module, and the optical module emitting a second optical signal to the interference module and then the interference module providing a first incident light and a second incident light to an object to be detected and a curved surface reference mirror respectively.

2. The light source module of claim 1, wherein the laser pump unit having a core pump structure needs a pump power ranging from 30 mW to 300 mW and a core diameter of the laser pump unit having the core pump structure ranges from 3 um to 20 um.

3. The light source module of claim 1, wherein the lens unit comprises a gradient-index (GRIN) lens.

4. The light source module of claim 1, wherein the fiber unit comprises an Yb-doped double-clad fiber, an Er-doped double-clad fiber, or a Tm-doped double-clad fiber.

5. The light source module of claim 1, wherein the laser pump unit has a pump structure including a core pump structure or a cladding pump structure, the laser pump unit has a core diameter, and the fiber unit has an Yb-doped fiber with a concentration of Yb ion; wherein a length of the fiber unit is related to the pump structure of the laser pump unit, the concentration of Yb ion in an Yb-doped fiber of the fiber unit, and the core diameter of the laser pump unit.

6. The light source module of claim 1, wherein the laser pump unit having a cladding pump structure needs the pump power ranging from 100 mW to 10 W and the core diameter of the laser pump unit having the cladding pump structure ranges from 10 um to 40 um.

7. The light source module of claim 1, further comprising:

a filter unit, disposed between the lens unit and the fiber unit, for enhancing an amplified spontaneous emission (ASE) of a forward direction from the lens unit toward the fiber unit by reflecting the amplified spontaneous emission of a reverse direction from the fiber unit toward the lens unit back to the fiber unit when the fiber unit receives the condensed beam.

8. The light source module of claim 1, further comprising:
an output end, for outputting the first optical signal; and
a filter unit, disposed between the fiber unit and the output end, for filtering the first optical signal before the first optical signal enters into the output end.

9. The light source module of claim 1, wherein when the laser pump unit has a core pump structure, the first optical signal is an amplified spontaneous emission (ASE) outputted by a core of the fiber unit; when the laser pump unit has a cladding pump structure, the first optical signal is a spontaneous emission collected and outputted by a cladding layer having larger numerical aperture of the fiber unit and the first optical signal fails to be amplified by stimulated emission.

10. A light source module operating method, for operating a light source module of an optical apparatus, the optical apparatus comprising an optical module and an interference module, and the optical module being disposed between the light source module and the interference module, the optical module comprising a collimating lens and a multi-mode fiber, the light source module comprising a laser pump unit, a lens unit, and a fiber unit, the laser pump unit comprising a butterfly package type laser diode, the method comprising steps of:
  (a) the laser pump unit generating a laser source;
  (b) the lens unit converting the laser source into a condensed beam; and
  (c) the fiber unit receiving the condensed beam and emitting a first optical signal to the optical module, and the optical module emitting a second optical signal to the interference module and then the interference module providing a first incident light and a second incident light to an object to be detected and a curved surface reference mirror respectively.

11. The method of claim 10, wherein the laser pump unit having a core pump structure needs a pump power ranging from 30 mW to 300 mW and a core diameter of the laser pump unit having the core pump structure ranges from 3 um to 20 um.

12. The method of claim 10, wherein the lens unit comprises a gradient-index (GRIN) lens.

13. The method of claim 10, wherein the fiber unit comprises an Yb-doped double-clad fiber, an Er-doped double-clad fiber, or a Tm-doped double-clad fiber.

14. The method of claim 10, wherein the laser pump unit has a pump structure including a core pump structure or a cladding pump structure, the laser pump unit has a core diameter, and the fiber unit has an Yb-doped fiber with a concentration of Yb ion; wherein a length of the fiber unit is related to the pump structure of the laser pump unit, the concentration of Yb ion in an Yb-doped fiber of the fiber unit, and the core diameter of the laser pump unit.

15. The method of claim 10, wherein the laser pump unit having a cladding pump structure needs the pump power ranging from 100 mW to 10 W and the core diameter of the laser pump unit having the cladding pump structure ranges from 10 um to 40 um.

16. The method of claim 10, further comprising a step of:
  enhancing an amplified spontaneous emission (ASE) of a forward direction from the lens unit toward the fiber unit by reflecting the amplified spontaneous emission of a reverse direction from the fiber unit toward the lens unit back to the fiber unit when the fiber unit receives the condensed beam.

17. The method of claim 10, further comprising a step of:
  filtering the first optical signal outputted by the fiber unit.

18. The method of claim 10, wherein when the laser pump unit has a core pump structure, the first optical signal is an amplified spontaneous emission (ASE) outputted by a core of the fiber unit; when the laser pump unit has a cladding pump structure, the first optical signal is a spontaneous emission collected and outputted by a cladding layer having larger numerical aperture of the fiber unit and the first optical signal fails to be amplified by stimulated emission.

* * * * *